(12) United States Patent
Agnew et al.

(10) Patent No.: US 9,474,514 B2
(45) Date of Patent: Oct. 25, 2016

(54) DEVICES AND METHODS FOR TREATING FISTULAE AND OTHER BODILY OPENINGS AND PASSAGEWAYS

(75) Inventors: Charles W. Agnew, West Lafayette, IN (US); Mark Duncan, Westfield, IN (US); Chad E. Johnson, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 554 days.

(21) Appl. No.: 13/247,156

(22) Filed: Sep. 28, 2011

(65) Prior Publication Data

US 2013/0079811 A1  Mar. 28, 2013

Related U.S. Application Data

(60) Provisional application No. 61/387,077, filed on Sep. 22, 2010, provisional application No. 61/500,238, filed on Jun. 23, 2011.

(51) Int. Cl.
| | | |
|---|---|---|
| *A61B 17/08* | (2006.01) | |
| *A61B 17/00* | (2006.01) | |
| *A61B 17/12* | (2006.01) | |

(52) U.S. Cl.
CPC ..... *A61B 17/0057* (2013.01); *A61B 17/12099* (2013.01); *A61B 17/12159* (2013.01);
CPC .............. *A61B17/1219* (2013.01); *A61B 17/12181* (2013.01); *A61B 2017/0065* (2013.01); *A61B 2017/00579* (2013.01); *A61B 2017/00601* (2013.01); *A61B 2017/00628* (2013.01); *A61B 2017/00641* (2013.01)

(58) Field of Classification Search
CPC ............ A61B 17/0057; A61B 17/12022; A61B 17/12027; A61B 17/12031; A61B 17/12036; A61B 17/1204; A61B 17/12045; A61B 17/12099; A61B 17/12109; A61B 17/12118; A61B 17/12145; A61B 17/12154; A61B 17/12159; A61B 17/12163; A61B 17/12168; A61B 17/12172; A61B 17/1219; A61B 2017/00575; A61B 2017/00579; A61B 2017/00592; A61B 2017/00597; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/00646; A61B 2017/00654; A61B 2017/00659; A61B 2017/00672; A61B 2017/00676; A61B 2017/0065; A61B 2017/1205; A61B 2017/12127; A61B 17/12104; A61B 17/12113; A61B 17/12112; A61B 17/12181; A61B 17/12186; A61B 2017/3437; A61B 1/121; A61B 1/122; A61B 1/126; A61F 13/15; A61F 13/20; A61F 13/2062; A61F 13/2065; A61F 13/6068; A61F 13/2071; A61F 13/2074; A61F 13/208; A61F 2013/15495; A61F 2013/15504; A61F 2013/15513; A61F 2013/1552; A61F 2013/15528; A61F 2013/15536; A61F 2013/15544; A61F 2013/1556; A61F 13/2051; A61F 13/2057; A61F 13/206; A61F 13/15203; A61F 13/2002; A61F 13/2005; A61F 13/2008; A61F 13/2011; A61F 13/2017; A61F 13/2022; A61F 13/36; A61F 13/38; A61F 2013/15512; A61F 2013/2014; A61F 2013/15024; A61F 2013/1513; A61F 2013/15121; A61F 2013/15008; A61F 2013/15146; A61F 2013/14154; A61F 2013/15195; A61F 2013/15463; A61F 2013/15741; A61F 2013/15487; A61F 2013/53081; A61F 2013/426; A61F 2013/530802; A61F 2013/530948; A61F 2013/530941; A61F 2013/530934; A61F 2013/530927; A61F 2013/530912; A61F 2013/530817; A61F 2013/530824; A61F 2013/530832; A61F 2013/530839; A61F 2013/530846; A61F 2013/530854; A61F 2013/530861; A61F 2013/530868; A61F 2013/530875; A61F 2013/50389; A61L 15/14; A61L 15/16; A61L 15/425; A61L 15/52; A47K 7/02; A47L 13/16; B08B 1/003
See application file for complete search history.

(56) References Cited

U.S. PATENT DOCUMENTS

| | | | | |
|---|---|---|---|---|
| 5,556,391 | A | * | 9/1996 | Cercone ............... A61F 13/36 602/46 |
| 5,662,681 | A | | 9/1997 | Nash et al. |
| 5,755,706 | A | * | 5/1998 | Kronenthal ............ A61F 13/20 604/358 |
| 2005/0192616 | A1 | * | 9/2005 | Callister et al. .............. 606/193 |
| 2005/0209633 | A1 | * | 9/2005 | Callister et al. .............. 606/200 |
| 2006/0041247 | A1 | * | 2/2006 | Petrosenko ............. A61F 13/00 604/543 |
| 2008/0132820 | A1 | * | 6/2008 | Buckman ........... A61B 17/1325 602/48 |
| 2009/0062846 | A1 | * | 3/2009 | Ken ............................. 606/213 |
| 2009/0069843 | A1 | * | 3/2009 | Agnew ........................ 606/213 |
| 2010/0241162 | A1 | * | 9/2010 | Obermiller et al. ......... 606/213 |

FOREIGN PATENT DOCUMENTS

| | | |
|---|---|---|
| WO | WO 2006/078578 A2 | 7/2006 |
| WO | WO 2009/029914 A1 | 3/2009 |

OTHER PUBLICATIONS

International Search Report dated Feb. 6, 2012 from related case, PCT/US2011/053483, pp. 1-7.

Written Opinion of the International Searching Authority, dated Feb. 6, 2012 from related case, PCT/US2011/053483, pp. 1-8.

* cited by examiner

*Primary Examiner* — Jonathan Miles
*Assistant Examiner* — Kendra Obu
(74) *Attorney, Agent, or Firm* — Woodard, Emhardt, Moriarty, McNett & Henry LLP

(57) ABSTRACT

Some aspects of the present invention are directed to unique products and methods for treating fistulae and other passageways and openings in the body. In some preferred forms, an inventive construct will include an elongate graft body that incorporates a plurality of sheet or sheet-like segments. The plurality of sheet or sheet-like segments, in some arrangements, will be stacked in a generally longitudinal direction along the length of the plug body, and optionally, the segments will be received over one or more elongate elements. Elongate elements of this sort can take a variety of forms including a suture, wire, filament, or other relatively thin-bodied elongate member, although in some forms, an elongate element will be or include a somewhat heftier structure such as a biodegradable or non-biodegradable three-dimensional body.

40 Claims, 6 Drawing Sheets

DEVICES AND METHODS FOR TREATING FISTULAE AND OTHER BODILY OPENINGS AND PASSAGEWAYS

REFERENCE TO RELATED APPLICATIONS

This application claims the benefit of U.S. Provisional Application No. 61/387,077, filed Sep. 28, 2010, and U.S. Provisional Application No. 61/500,238, filed Jun. 23, 2011, both of which are hereby incorporated by reference.

BACKGROUND

The present invention relates generally to medical technology and in particular aspects to methods and systems for addressing fistulae and other passageways and openings in the body. As further background, there exist a variety of passageways and openings in the body which can be plugged, blocked or otherwise occupied by medical implants and materials to provide benefit to the patient. For example, it may be desirable to plug or otherwise treat a fistula. A variety of fistulae can occur in humans. These fistulae can occur for a variety of reasons, such as but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

When surgery is deemed necessary, one operation for fistula closure is resection of the fistula-bearing segment and primary end-to-end anastamosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices and methods for addressing fistulae and other passageways and openings in the body. The present invention is addressed to those needs.

SUMMARY

The present invention provides, in certain aspects, unique methods and systems for treating fistulae and other passageways and openings in the body. In one embodiment, a medical implant comprises an elongate implant body that includes a plurality of sheet or sheet-like elements stacked or otherwise overlapping one another in a generally longitudinal direction along the length of the implant body. In some forms, each of the elements will generally have a top surface, a bottom surface and at least one side edge. This side edge, in some particularly preferred forms, will have a greater surface porosity than the element's top and bottom surface. The invention also provides methods for manufacturing such implants, and in some embodiments, inventive methods include locating this sort of implant in a fistula tract or other passageway or opening in the body.

In another embodiment, this sort of medical implant is a plug or plug-like device that is specifically adapted for treating a fistula and comprises an elongate plug body that includes a plurality of sheet or sheet-like segments. Each of the segments will generally have a top surface, a bottom surface and at least one side edge. This side edge, in some particularly preferred forms, will have a greater surface porosity than the segment's top and bottom surface, and the sheet segments will be stacked in a generally longitudinal direction along the length of the plug body. Optionally, the plug or plug-like device will also incorporate one or more separately-elongate elements (e.g., a suture, three-dimensional plug, etc.) over which the sheet segments are received. While in some forms all of the sheet segments will be essentially identical in terms of their size, shape, material (s) of construction, etc., in some other forms, any one segment might vary with respect to another segment in one or more ways. The invention also provides methods for manufacturing such medical products, and in some embodiments, inventive methods include locating this sort of plug or plug-like device in a fistula tract or other region in the body.

Another aspect of the present invention provides a medical implant (e.g., a fistula plug) including a plurality of sheet, layer or other material segments. These segments are stacked adjacent one another in succession and held together as a stack to provide an elongate plug or other implant body for subsequent implantation in the body of a patient. The stack extends in a generally longitudinal direction along the plug body with adjacent edges of the stacked layers forming a substantial portion of the side exterior surface of the plug body.

A further aspect of the invention provides a fistula plug or other implantable plug device or body which includes a stack of material layers. Each of the layers has a top surface, a bottom surface and a perimeter edge that separates the top surface from the bottom surface. The stack extends in a generally longitudinal direction along the length of the plug body so that the perimeter edges of the stacked layers extend in a generally lateral direction across the plug body. In some preferred forms, the combined perimeter edges will form a substantial portion of the side exterior surface of the plug body. Illustratively, the combined perimeter edges of the stacked layers might provide more than about 50% of the side exterior surface of the plug body, and in some constructions at least about 80% to essentially 100% of the side exterior surface of the plug body.

Another embodiment of the invention provides a medical implant (e.g., a fistula plug) that includes an elongate three-dimensional plug member which provides an inner core. The medical implant further includes a plurality of sheet segments which each have an opening through which the inner core can be received. The sheet segments are received over the inner core and are stacked adjacent one another in succession along the inner core such that the plurality of sheet segments extend over a substantial length of the inner core.

Yet another embodiment of the present invention provides a fistula plug which includes a plurality of disks that are stacked adjacent one another in succession and held together to provide an elongate plug member. Each of the disks comprises multiple stacked layers of an extracellular matrix material that are harvested in layer form from a biological tissue source. In one embodiment, such layers when in a substantially dry state will generally have a thickness in the range of about 80 microns to about 120 microns.

Yet another embodiment of the present invention provides a fistula plug which includes a plurality of individual sheet segments that are stacked adjacent one another in succession and held together to provide an elongate plug member which has a length of about 2 cm to about 20 cm and a maximum width of about 5 mm to about 20 mm. In some forms, such an elongate plug member will have about 5 to about 25 stacked segments per centimeter along the length of the plug member.

Still another aspect of the present invention provides a medical implant that comprises an elongated sheet or sheet-like structure that is folded back and forth upon itself in a longitudinal direction along the length of the structure to form a three-dimensional implantable body.

In one inventive embodiment, a three-dimensional implantable body incorporates a sheet or sheet-like material (e.g., comprising an isolated layer of ECM material) that is folded back and forth upon itself to provide a stack of sheet or sheet-like segments with the stack extending in a generally longitudinal direction along the length of the three-dimensional implantable body. Such a three-dimensional implantable body can have any suitable length and in some instances will be about 2 cm to about 14 cm long. In these and other embodiments, the stack of sheet segments can include about 2 sheet segments per centimeter to about 30 sheet segments per centimeter along the length of the implantable body, or about 4 sheet segments per centimeter to about 12 sheet segments per centimeter along the length of the implantable body.

Other objects, embodiments, forms, features, advantages, aspects, and benefits of the present invention shall become apparent from the detailed description and drawings included herein.

DETAILED DESCRIPTION

Figure 1:
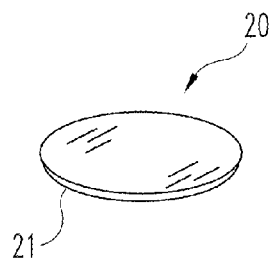
FIG. 1 is a perspective view of a graft element according one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique products and methods for treating fistulae and other passageways and openings in the body. In some preferred forms, an inventive construct will include an elongate graft body that incorporates a plurality of sheet or sheet-like segments. These segments, as will become apparent, can be shaped and configured in a variety of manners and can be formed with one or more of a variety of naturally-derived and/or non-naturally derived materials.

While not necessary to broader aspects of the invention, in some arrangements, the plurality of sheet or sheet-like segments will be stacked in a generally longitudinal direction along the length of the plug body, and optionally, the segments will extend along, e.g., they will be received over, one or more elongate elements. Elongate elements of this sort can be constructed with one or more of a variety of naturally-derived and/or non-naturally derived materials and can take a variety of forms including but not limited to a suture, wire, filament, or other relatively thin-bodied elongate member, although in some forms, an elongate element will be or include a somewhat heftier structure such as a biodegradable or non-biodegradable three-dimensional body.

Continuing with a discussion of sheet materials useful in certain aspects of the present invention, in some forms, a sheet or sheet-like segment will be or include a material that is manufactured (e.g., by extrusion, in a mold or form, etc.) so as to exhibit essentially a unitary sheet-like structure, or it may be or include a material that is obtained from a natural source (e.g., harvested from a biological tissue source) to retain, at least in part, its native structure. In alternative forms, a sheet or sheet-like structure will incorporate many small filaments, strands or other smaller pieces of material that are interconnected or otherwise associated with one another to form a substantially unitary sheet-like construct. When utilized, these smaller pieces may or may not be bonded or directly connected to one another.

Suitable sheet segments, in some aspects of the present invention, will exhibit a flexibility or compliancy or they can be essentially non-flexible or non-compliant, in whole or in part. Sheets and other sheet-like structures can be essentially flat in a relaxed condition, or they can exhibit curvature and/or other non-planar features, for example, exhibiting a curved, convex or other three-dimensional configuration. A sheet or sheet-like element, in some embodiments, will include multiple layers of material. When a sheet is multilayered, the constituent layers may all be identical, or any one layer may be the same or different than any other layer in terms of its material(s) of construction and/or any other characteristic.

In some preferred forms, a sheet or sheet-like segment will have a top surface, a bottom surface and at least one side edge. This side edge or any other side edge can be shaped and configured in a variety of fashions. FIG. 1 shows a sheet-like segment according to one embodiment of the present invention. This relatively thin, disk-like element 20 has a generally circular perimeter edge 21. The thickness of this and other graft segments or bodies, in some preferred forms, will incorporate multiple layers or pieces of material, e.g., up to 50 or more layers of material. In some preferred embodiments, a multilayered element will incorporate from about 2 to about 40 layers of material, or about 2 to about 20 layers of material, or about 4 to about 12 layers of material, or about 4 to about 8 layers of material. Such layers, for example, might be formed with, or otherwise incorporate, a reconstituted or non-reconstituted collagenous material. Illustratively, an individual segment like the one shown in FIG. 1 might include a multilayered extracellular matrix (ECM) material that has been formed by stacking and/or folding one or more pieces of an ECM material.

Suitable multilaminate structures can include a plurality of ECM layers bonded together, a plurality of non-ECM layers (e.g., biodegradable or non-biodegradable synthetic polymer layers) bonded together, or a combination of one or more ECM layers and one or more non-ECM layers bonded together. Illustratively, two or more ECM segments can be bonded together using a bonding technique, such as chemical cross-linking or vacuum pressing under dehydrating conditions. An adhesive, glue or other agent may also be used in achieving a bond between material layers. Suitable bonding agents may include, for example, collagen gels or pastes, gelatin, or other agents including reactive monomers or polymers, for example cyanoacrylate adhesives. A combination of one or more of these with dehydration-induced bonding may also be used to bond ECM material layers to one another.

Figure 2:
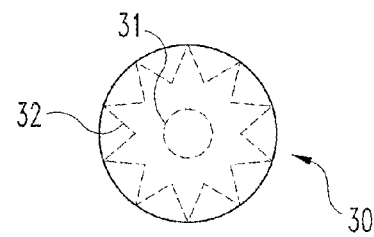
FIG. 2 is a top view of a graft element according another embodiment of the present invention.

While circular segments will be useful in certain aspects of the present invention, a sheet or sheet-like segment can exhibit a variety of non-circular shapes as well. Accordingly, perimeter and non-perimeter regions of a somewhat more generic segment such as that shown in FIG. 1 (or any region of a raw material sheet) can be further manipulated to transform the piece into a desirable shape. Another example of a sheet-like segment 30 that will be useful in certain aspects of the present invention is shown in FIG. 2. In this illustration, the exemplary dotted lines indicate how, for example, the perimeter edge of a substantially circular segment might instead be made non-circular, and how the segment could be outfitted with a central opening 31. Once transformed in this manner, the periphery of the disk-like member will boast a plurality of projections 32 giving the member an overall saw-toothed or star-like shape. These types of projections, when incorporated into sheet or sheet-like segments of the present invention, can exhibit a variety of shapes including some having rectilinear and/or curvilinear features.

Figure 3A:
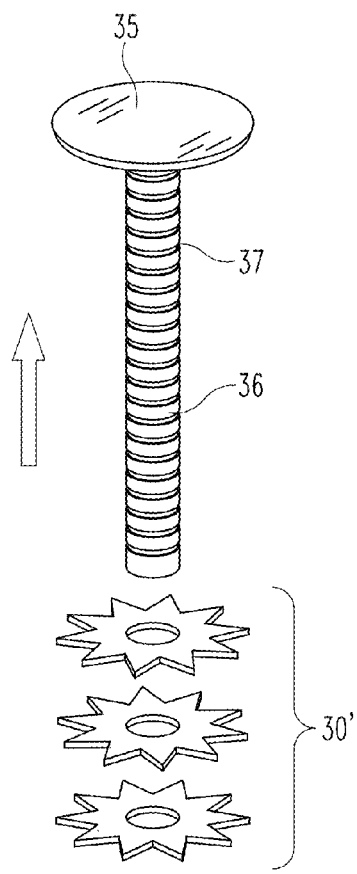
FIG. 3A is a perspective view a graft product being assembled according to one embodiment of the present invention.

While not necessary to broader aspects of the invention, in some embodiments, a stack of sheet or sheet-like segments will be made to extend in a longitudinal direction along one or more separately-elongate elements. With reference now to FIG. 3A, shown is an example of how an illustrative graft product might be assembled according to one embodiment of the present invention. This particular device includes an optional disk-like capping member 35 at one end, and an elongate and generally solid cylindrical plug body 36 that extends away from the capping member. In some preferred forms, plug body 36 will incorporate a remodelable material such as a remodelable ECM material. Several sheet segments, which have been shaped according to the pattern shown in FIG. 2, are ready to be received over the plug body in the direction shown. Each of the sheet segments 30' has a non-circular perimeter 31', and also a central circular opening 32' through which the elongate cylindrical plug body 36 can be received. Optionally, this sort of core-like member might be outfitted with a series of generally lateral grooves or cuts in an exterior surface of the plug body for receiving one or more sheet or sheet-like graft elements. Illustrative grooves 37 extending in a generally circumferential fashion around plug body 36 are shown in FIG. 3A. The number of grooves, their shape and their relative spacing can be adjusted as desired. Also, such grooves might be cut sufficiently deep, for example, to keep the members spaced apart and in place along the plug. Such adaptations might be particularly useful when used to accommodate a graft element having inner projections like those shown in FIG. 6A.

Continuing with FIG. 3A, while plug body 36 is generally cylindrical, such bodies can have a variety of shapes and configurations. Whether cylindrical or non-cylindrical, a plug body or core-like member can, for example, have a general diameter of about 0.5 mm to about 24.0 mm and a length of about 0.5 cm to about 30 cm, although larger or smaller values for these dimensions can be used. A plug body in some forms of the invention will include a portion having a general diameter ranging from about 1.0 mm to about 15.0 mm, or from about 1.5 mm to about 12.0 mm, or from about 2.0 mm to about 8.0 mm, and a length ranging from about 2.0 cm to about 24.0 cm, or from about 3.0 cm to about 15.0 cm, or from about 4.0 cm to about 12.0 cm. Expandable plug bodies will be utilized in some embodiments.

Such a plug body can have a constant or varying cross-sectional area along its length. Illustratively, a plug body, or any portion thereof, can exhibit a generally cylindrical shape, a conical shape or any other suitable shape including some that have tapered and/or non-tapered longitudinal portions. Thus, for example, plug body 36 instead could be tapered along its length (in either direction) and optionally the openings in the sheet segments instead could be made different sizes to accommodate the changes in the plug diameter. As well, a cross section of a particular portion of a body can exhibit a variety shapes including some that have rectilinear and/or curvilinear features. Thus, a body can include a portion having a generally circular or non-circular (e.g., elliptical, square, star-shaped, hexagonal, etc.) cross section. Additionally or alternatively, a body can include various other three-dimensional volumetric body portions such as but not limited to braids, tubes, hemi-cylinders, strands, threads, strips and other shaped body portions having suitable dimensions.

Such plug bodies and other implant components described herein can be formed with one or more of a variety of naturally derived and/or non-naturally derived materials, and they can be constructed in any suitable manner including but not limited to by extrusion, using a mold or form, formation around a mandrel, and/or combinations or variations thereof. In some embodiments, an implant body is formed with a reconstituted or otherwise reassembled ECM material such as a highly expandable ECM foam or sponge material. Implant bodies can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive implant component is constructed by randomly or regularly packing one or more pieces of single or multilayer ECM sheet material within a mold and thereafter processing the packed material.

Figure 3B:
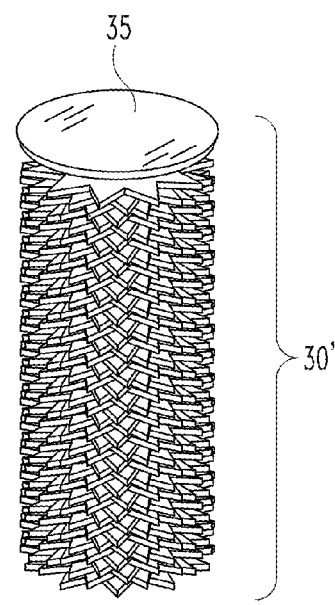
FIG. 3B is a perspective view an inventive graft product.
Figure 7:
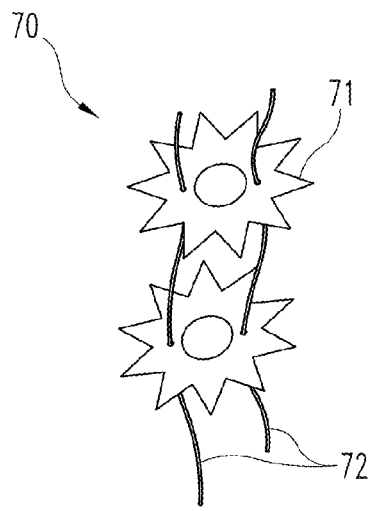
FIG. 7 is a partial, perspective view of another inventive graft product.

FIG. 3B shows the product from FIG. 3A at a further stage of assembly. A plurality of segments 30' have now been received on plug body 36. The segments extend over a substantial length of the plug body, and in doing so, essentially cover it. By having a large number of closely-packed segments extending in a generally longitudinal direction along the length of the plug body, the combined perimeter edges of the stacked segments provide a substantial portion of the side exterior surface of the plug body. In some inventive constructions, essentially the entire side exterior surface of a plug body will be provided by edge portions of stacked segments extending in a generally longitudinal direction along the length of the plug body. As another illustrative example of multiple segments received over or along a separately-elongate element, FIG. 7 shows a plurality of sheet segments 71 interconnected through their mutual receipt over a pair of suture pieces 72.

A stack of segments can include any suitable number of segments. In some instances, the number of segments occurring in a stack will be influenced by factors like the thickness of the individual segments, whether any of the segments exhibit compressibility, and the like, although a number of other factors can influence how many segments will be necessary or desirable for a given application. Some inventive stacks will have up to 50 or more single- or multilayer segments per centimeter along the stack. In some preferred embodiments, a stack will have from about 0.2 to about 40 segments per centimeter along the stack, or from about 2 to about 30 segments per centimeter along the stack, or from about 6 to about 24 segments per centimeter along the stack, or from about 10 to about 20 segments per centimeter along the stack. Such stacks will generally have a length in the range of about 1.0 cm to about 30 cm, although larger or smaller values for these dimensions can be used. A stack in some forms of the invention will have a length ranging from about 2.0 cm to about 24.0 cm, or from about 3.0 cm to about 15.0 cm, or from about 4.0 cm to about 12 cm.

When used in the treatment of a fistula or other bodily passageway, in some instances, the plurality of segments 30' will be constructed and arranged such that they will be able to deflect somewhat longitudinally as they pass through the opening or passageway which will allow the graft to attain a lower profile during delivery. This is possible even when the segments are fused together to some degree. In some forms, one or more segments will be somewhat stiff to allow the projections 32 to act as a sort of barbed member when forced against a wall of tissue during deployment. A particular segment might be provided, for example, by a vacuum pressed or air dried multilaminate collagenous material. In one preferred embodiment, at least one of the segments will be formed with a somewhat stiff ECM material. This segment will be able to deflect somewhat longitudinally when the graft is forced through a fistula tract in a first direction. However, when the graft is forced in the opposite direction in a later delivery step, the stiff segment will deflect back to some degree causing the projections 32 to engage, and in some instances to even penetrate into, the wall of the fistula tract and provide some level of fixation within the tract.

In some versions of the FIG. 3B product, it will be advantageous for an edge region of a sheet-like segment to have a greater surface porosity than the segment's top and bottom surface, and it will be particularly advantageous for at least one of the constituent segments, and preferably all of the segments, to incorporate a remodelable material exhibiting this quality. Illustratively, such remodelable materials can be provided by collagenous materials obtained from a warm-blooded vertebrate, and especially a mammal. Remodelable ECM tissue materials harvested as intact sheets from a mammalian source and processed to remove cellular debris can be advantageously processed to retain at least a portion, and potentially all, of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when an inventive construct incorporates this sort of material, cells will invade the remodelable material upon implantation eventually leading to the generation of newly-remodeled, functional tissue.

Figure 4:
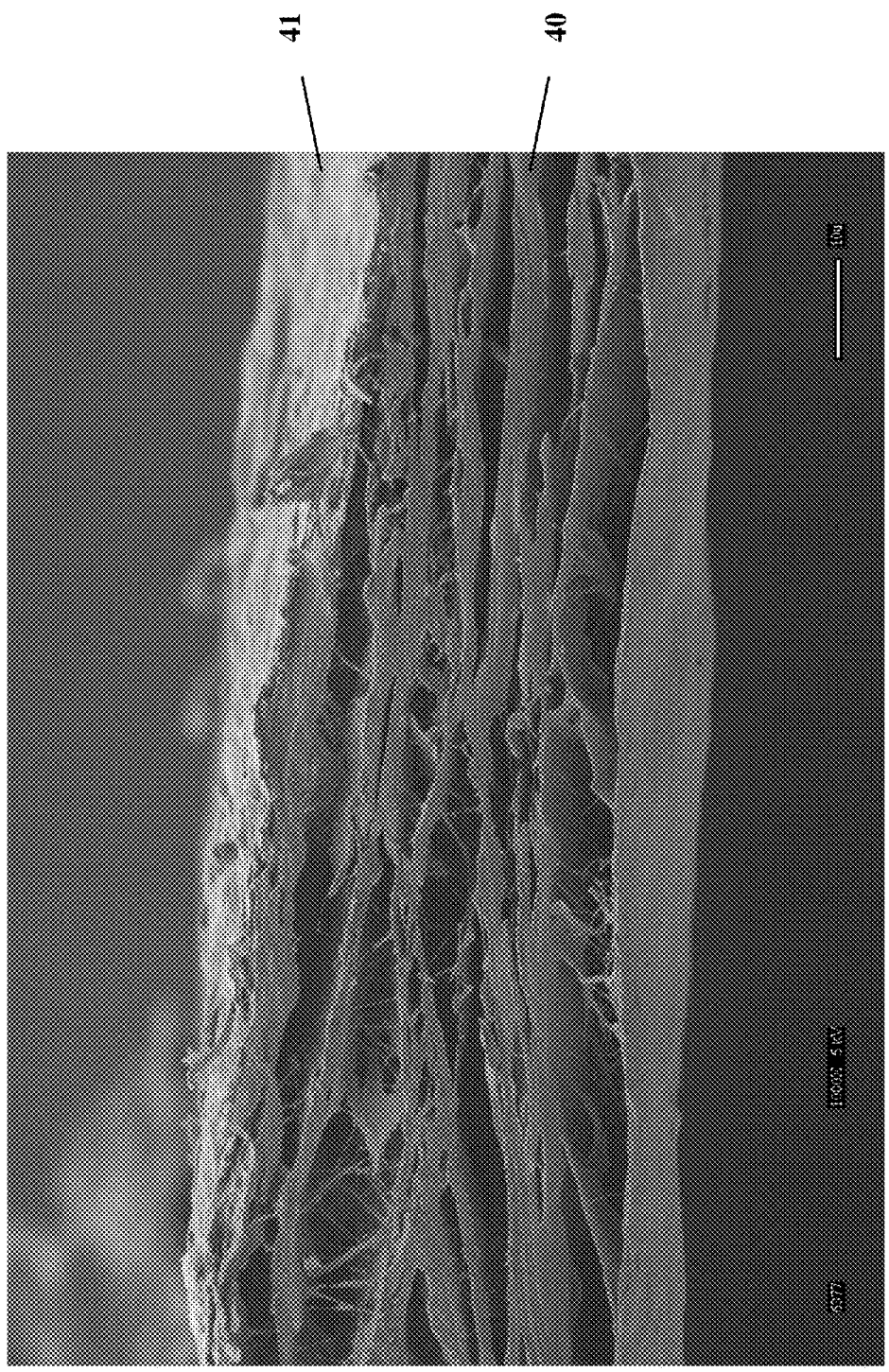
FIG. 4 is an image of a graft material useful in certain embodiments of the present invention.

FIG. 4 is a photomicrograph taken by scanning electron microscopy and shows an edge of a submucosal ECM material. As can be seen, the side edge 40 of the material has pockets and cavernous regions within the native microarchitecture which allows for the easy migration of cells into the inner regions of the matrix to promote integration of the graft material and wound healing. A less porous top surface 41 of the material can also been seen in the illustrative layer. The side edge provides an advantageous pathway for cells and other bodily substances to enter and populate the matrix, as opposed to the less porous and less inviting top and bottom surfaces. Moreover, the graft material can be processed to retain at least some of its native biologic components that effect cell response, including heparin sulfate, hyaluronic acid, and fibronectin. These materials, remaining in the graft, will even more advantageously promote migration and development of the cells when they are able to enter through the edge portions of the material.

It is possible, and in some instances quite advantageous, to construct a sheet or sheet-like segment like those shown in FIG. 1 or 3A so that at least one side edge of the segment is formed, at least in part, by a side edge of an ECM material. In some preferred forms, essentially the entire perimeter edge of a sheet-like segment will be formed by an edge of an ECM material, for example, where multiple pieces of an ECM material like the one shown in FIG. 4 are laid atop one another and fused together to form a multilayered segment having side edges that are provided by adjacent side edges 40 of the overlapping ECM layers.

If such segments are used, for example, in the construction of the graft depicted in FIG. 3B, it becomes apparent that the side exterior surface of the resulting plug body will be quite densely packed with exposed edge portions of the segments, and consequently, exposed edge portions of the ECM materials. With such an arrangement, the exposed ECM edges will extend vertically and horizontally along the graft. The numerous exposed ECM edges will provide an abundance of openings and passages for cells and other bodily substances to easily enter the microarchitectures of the ECM materials, and once in, the bioactive agents retained in the matrices will induce migration and proliferation of the cells within and between the individual graft segments so as to promote integration and replacement of the segments, and of the plug body as a whole, with newly-remodeled patient tissue. Notably, with all else being equal, the perimeter edge of the star-shaped segment in FIG. 3A is longer, and thus provides more edge surface area, than the perimeter edge of the circular segment in FIG. 1.

Referring again to FIG. 3B, in this particular illustrative embodiment, all of the individual sheet segments 30' are essentially identical. However, in alternative inventive constructs having multiple sheet or sheet-like segments, any one segment can vary with respect to another segment in terms of its size, shape, material(s) of construction and/or any other physical or other characteristic. Illustratively, if two sheet segments are formed from essentially the same material(s) initially, one of the segments might be physically, chemically, biologically and/or otherwise modified prior to implantation. Accordingly, specific types of segments can be placed at particular locations along the plug body, and in this regard, the location selected for a particular type of segment might be dictated by advantages expected to result from having that segment reside at a particular location at the eventual treatment site (e.g., at or near a fistula opening or at any other specific location in a fistula or other bodily passageway or opening). As one example, sheet segments within a single plug can have different densities, degrees of stiffness, and/or coatings or other incorporations such as drug (antimicrobial, anti-inflamatory, etc.) or radiopaque components. Illustratively, a graft might include some segments that are formed with a naturally derived material such as a harvested ECM material and other segments that are formed with a non-naturally derived material such as a biodegradable synthetic polymeric material. In some forms, a naturally derived material and a non-naturally derived material will be used in the formation of a single sheet or sheet-like segment within an inventive graft. As another example, a graft might include some ECM segments that are somewhat stiff and thus potentially helpful for fixation purposes, and also some other ECM segments that are less stiff (e.g., less dense) and thus potentially more receptive to tissue ingrowth and better for incorporation purposes. While such combinations will certainly be useful in some applications, it is merely illustrative of the many possible sheet segment combinations falling within the scope of some aspects of the present invention. In some instances, a fistula tract or other treatment site will be mapped or otherwise analyzed prior to receiving an inventive graft construct therein, and the number of sheet segments and their individual properties will be selected based on this analysis, for example, to optimize healing in different regions or zones of a fistula tract based on an initial analysis or estimate.

When an inventive construct includes multiple stacked sheet segments like those shown in FIG. 3B, and when those segments include a collagen-containing material, the bottom surface of one collagenous segment might be in direct contact with the top surface of another collagenous segment. While the extent and types of contact between such surfaces can vary, in certain forms, two collagen-containing surfaces will be fused together or otherwise connected to form a more interconnected graft body. When two collagenous surfaces are in contact with one another, certain types of advantageous bonding or fusing can occur between them. Thus, in some embodiments, an illustrative construct like the one shown in FIG. 3B will have collagen-containing segments 30', and some or all of these segments will be fused together. This construct, while more uniform, will still have a side exterior surface with significant exposed ECM edge portions.

When an inventive construct includes multiple collagen-containing portions, in certain embodiments, these portions will desirably be of a character so as to form an attachment to one another by virtue of being dried while compressed against each other. For example, a graft can include multiple collagen-containing sheets or segments, and dehydration of these materials in forced contact with one another can effectively bond the materials to one another, even in the absence of other agents for achieving a bond, although such agents can be used while also taking advantage at least in part on the dehydration-induced bonding. With sufficient compression and dehydration, the two collagenous materials can be caused to form a generally unitary collagenous structure. Vacuum pressing operations, and the closely bonded nature that they can characteristically impart to the collagen-containing materials, are highly advantageous and preferred in these aspects of the invention.

A variety of dehydration-induced bonding methods can be used to fuse ECM portions together. In one preferred embodiment, multiple layers or other pieces of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon an ECM material, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Figure 5:
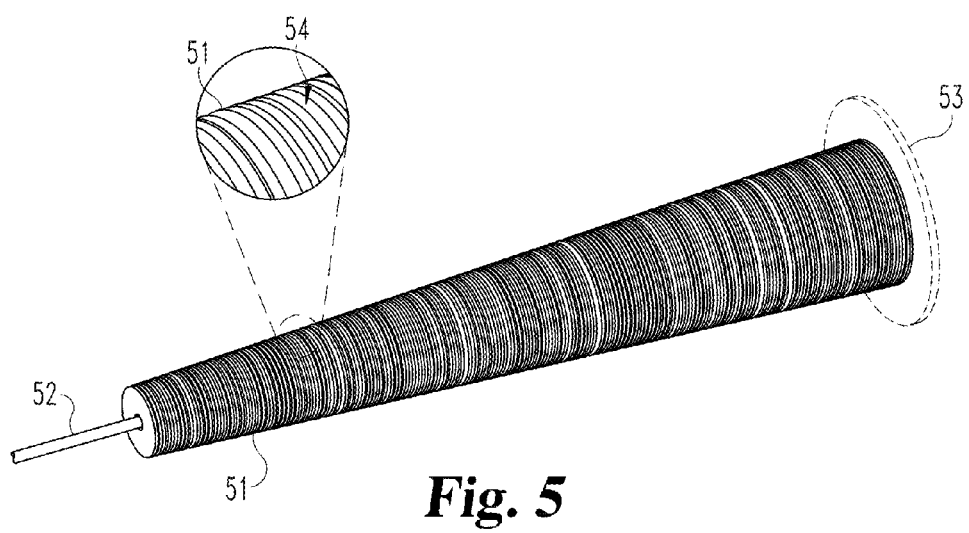
FIG. 5 is a perspective view of another inventive graft product.

With reference now to FIG. 5, shown is a graft product 50 according to another embodiment of the present invention. Product 50 includes a plurality of generally circular graft elements 51. Each of the elements is formed with one or more layers of material such as the submucosal ECM material shown in FIG. 4, and each is equipped with a central opening through which a relatively thin elongate structure 52 can be received for stacking the elements along the elongate structure as shown. By varying the diameters of the elements along the plug, a conical or tapered plug is formed. Such assemblies, whether having constant or varying cross-sectional areas along their lengths, will generally have a maximum or average diameter in the range of about 2.0 mm to about 30.0 mm, and a length in the range of about 0.5 cm to about 30 cm, although larger or smaller values for these dimensions can be used. A graft assembly in some forms of the invention will have a maximum or average diameter ranging from about 3.0 mm to about 24.0 mm, or from about 3.5 mm to about 15.0 mm, or from about 4.0 mm to about 12.0 mm, and a length ranging from about 2.0 cm to about 18.0 cm, or from about 3.0 cm to about 15.0 cm, or from about 4.0 cm to about 12.0 cm.

Continuing with FIG. 5, in some embodiments, this sort of stacked arrangement will be formed prior to delivering the graft product to an implant site, and in these instances, the graft elements may or may not be directly connected to one another. The graft elements will be loosely held together along structure 52 in some constructions. FIG. 5 includes an enlarged view showing a type of construction where the graft elements are collectively held together yet there are small void or gaps 54 between adjacent surfaces of the material pieces. Even when quite small, these types of gaps can enhance the ability of cells and other bodily substances to infiltrate into interior regions of the overall plug body. Such arrangements can be particularly advantageous when the individual graft elements are made to have slits or other exposed edge portions in interior regions of the elements such as in FIGS. 6A-6D.

In some other forms, a stacked arrangement like that shown in FIG. 5 will be formed, at least in part, at an implant site. Illustratively, the elongate structure 52 might be positioned in a fistula tract and thereafter graft elements, or a separate delivery instrument specifically adapted to carry such graft elements and track along the structure 52, will be delivered into the tract. Illustratively, a fistula might have a first opening, a second opening and a fistula tract extending therebetween, and in some of these embodiments, an anchored suture or other similar anchorable member having a relatively slender profile will be provided that extends from at or near the first fistula opening and through the fistula tract toward the second fistula opening. When it is a suture being anchored, the suture may be bonded or directly joined to tissues around the fistula, for example, by looping the suture through and around tissue at or near a fistula opening. Optionally, a fill substance can be injected or otherwise delivered into the fistula tract before, during or after introduction of any graft element. Such fill substances can include a variety of biodegradable and/or non-biodegradable materials as discussed elsewhere herein including flowable and non-flowable materials. In some instances, the second fistula opening will be fully or partially closed off following the delivery of such graft materials into the tract.

An anchorable element such as elongate structure 52 can be anchored in a variety of fashions including some that utilize glues or other bonding agents, tissue welding techniques, friction fitting or lodgment of an anchoring member, use of hooks, barbs, pins, single- and multiple part fasteners and/or other suitable anchoring modes as discussed elsewhere herein. Illustratively, a suture, cord, filament, plug-like core, etc. or other relatively thin-bodied elongate structure for receiving one or more graft elements may extend from a deployed anchoring member. Any suitable anchoring device or adaptation may be utilized in this regard. Some of these anchoring devices will be designed to penetrate into surrounding tissues and others will not. In some instances, in addition to providing an anchoring function at a treatment site, an anchoring member will serve one or more additional functions there. For example, an anchoring member might also be effective to temporarily or permanently cover, plug, block, fill, close or similarly affect a fistula passageway or opening, or any segment thereof, by virtue of its presence in and/or around the fistula. Additionally, when this sort of anchored suture has a free end that extends toward a second fistula opening, and potentially through the second opening, this free end might be left to freely hang in the fistula tract or it might be anchored to tissue at or near the second opening and/or connected to an anchoring member positioned at or near the second opening.

Optionally, for certain treatment applications such as the treatment of a fistula, the graft product will additionally incorporate a capping member 53 (shown in phantom) from which the plurality of graft elements will extend along the elongate structure. Capping member 53 in this illustrative embodiment is generally disc-shaped, and when adapted for treating a fistula, it can be sized for contacting portions of a tissue wall adjacent an opening to the fistula so as to inhibit its passage through the fistula opening. Such members can be formed with one or more of a variety of biodegradable and/or non-biodegradable materials as discussed elsewhere herein. In some preferred forms, the anchorable body is configured to at least partially block off fluid flow through the opening, and in some instances, to essentially seal off the opening from the passage of fluid. In some cases, holding capping member 53 in place over the fistula opening will be accomplished, at least in part, by applying tension to elongate structure 52 and maintaining this tension. Additionally or alternatively, member 53 can be bonded or otherwise attached to tissue around the opening, and in some forms, incorporate barbs or other adaptations to penetrate into tissue around the fistula to at least help hold the capping member in place. Further, in instances where it is necessary or desirable to deliver capping member 53 through the fistula tract, e.g., from a second opening, the body can be made compressible or otherwise deformable, for example, so that it can be folded, rolled, collapsed and/or otherwise compacted to a lower-profile condition for traversing the tract.

When a capping member relies, at least in part, on its size and shape to inhibit it passage through a bodily opening, this sort of member can be shaped and configured in a variety of manners. These include but are not limited to various three-dimensional shapes having rectilinear and/or curvilinear features. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.).

Penetrating and non tissue-penetrating anchorable members can be or include various types of frame and frame-like elements. These include single- and multiple-part devices. In some forms, a frame member will include a filament or wire body or other similar frame or frame-like support structure. Frame members, in some embodiments, can be designed to move between a first condition and one or more other conditions, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand.

Frames of this sort and other similar support elements useful in the present invention can be constructed using one or more pieces of superelastic wire or any of a variety of other suitable materials described herein or otherwise known to those skilled in the art including MRI compatible materials. Frames and other similar expandable and non-expandable support members, when utilized in the present invention, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

Figure 6A:
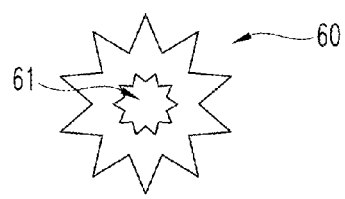
FIG. 6A is a top view of a graft element according one embodiment of the present invention.

With reference now to FIG. 6A, shown is a sheet segment 60 which is similar to those shown in FIG. 3A except that it has a non-circular central opening 61. If such a sheet segment was to be received over an elongate cylindrical plug body like the one shown in FIG. 3A, the inward-pointing projections occurring along the edge of the central opening 61, if properly sized, could act to grip the plug body to at least help retain the sheet segment on the plug body. Further, having an opening with this sort of convoluted shape can provide an inner edge with greater edge surface area as compared, for example, to a similarly-sized circular opening since the overall length of the edge is greater. Such openings, whether centrally or non-centrally located in a sheet segment, can exhibit a variety of shapes and configurations including some that exhibit curvilinear and/or rectilinear features such as oval, square, rectangular, star or diamond-shaped openings just to name a few.

Openings and passages in a sheet or other base structure can exhibit a variety of shapes and configurations. The angle at which an opening extends into and/or trough a material can vary as desired. When a sheet or other component includes a plurality of openings, all of the openings may be of the same type, or alternatively, any one opening may be shaped and configured differently than any other opening. An opening can be a slit or a non-slit opening. Spacing between or among openings can vary across a surface. Openings can be arranged in a pattern of some sort, or an arrangement of openings can be fully or partially randomized in a component. Some embodiments will include rows or lines of openings, although other recognizable groupings of openings can be employed as well. In certain embodiments, an opening will provide a pathway through a sheet-like segment or other structure for receipt of an elongate member.

A sheet or sheet-like material when used in the invention can have one or more slit or non-slit openings that extend into and/or through the material, and these openings may be located in various regions of the material. In certain embodiments, it may be advantageous to process a sheet or layer, or any portion thereof, so that it exhibits a meshed structure. One such graft element is shown FIG. 6B. Graft element 62 has a plurality of slits 63 in the graft material providing a meshed pattern. Each slit provides a pair of opposing edges.

Illustratively, such a mesh pattern can be useful to provide deformability to the structure, and in some case, expandability. In this regard, in some meshed constructs, expansion or other deformation of the structure will widen the openings created by the slits of the mesh pattern, by lateral and/or vertical displacement of the edges of the slits relative to one another. Certain meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the structure, particularly in situations where deformability and/or expandability provide advantages.

A meshed pattern can be created using suitable meshing devices designed for processing skin autograft sections. Such devices can include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-throughput method of preparing meshed material layers or constructs used in the invention. It will be understood, however, that the mesh pattern can be made by hand-cutting the material or by using appropriate cutting tools with multiple blades to cut the slits to provide the mesh pattern.

Figure 6B:
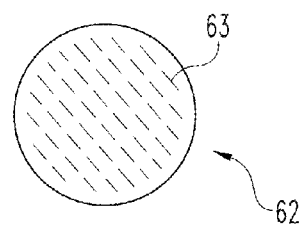
FIG. 6B is a top view of a graft element according another embodiment of the present invention.

Continuing with FIG. 6B, in this particular embodiment, the slits extend fully or partially through the material from top to bottom. When the graft element is formed with a submucosal or other ECM material such as that shown in FIG. 4, these slits will provide a multitude of sites at which cells will be able to easily invade and populate the matrix from edge portions of the slits in the graft material, as opposed to having to go through the non-slit top and bottom surfaces of the material. Such a pattern of slits provides, among other things, a greater density of edge portions across the material to provide even more sites for the efficient infiltration of cells and other bodily substances into the material upon implantation. In a fistula plug, providing a remodelable material with a greater amount of edge density can lead to a more effective remodeling of the material and closure of the fistula.

Figure 6C:
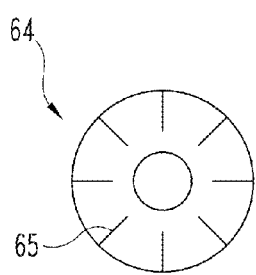
FIG. 6C is a top view of a graft element according another embodiment of the present invention.

In some embodiments, generating further edges within an existing structure such as by incorporating slits or other openings into a sheet or sheet-like segment as illustrated in FIGS. 6B and 6C will be effective to increase the number of edges or the edge density occurring in the structure. For example, without the slits 63 in FIG. 6B, the only edge occurring in the graft element 62 would be along its circular perimeter, and the length of this edge would be generally equal to the element's diameter multiplied by π (3.1416). With the addition of the slits, however, the quantity and sum total length of the edges occurring in the material are increased dramatically. In this regard, in some constructions, an existing graft element will be shaped and otherwise manipulated to increase the sum total length of its edges by at least about 10%. In some preferred forms, the sum total length of the edges will be increased in the range of about 20% to about 1000% or more, or in the range of about 25% to about 500%, or in the range of about 40% to about 300%, or in the range of about 50% to about 200%, or in the range of about 60% to about 150%.

A sheet or other structure can have any suitable number of slit or non-slit openings, and these openings may or may not be located across all parts of the sheet. With some sheets, openings will occur exclusively or primarily in peripheral regions of the sheet, although openings and passages can additionally or alternatively occur in non-peripheral regions of the sheet. As well, an opening may or may not be pre-existing in a sheet or other component. In instances where a fully or partially manufactured sheet is utilized in the invention, the sheet can be manufactured so as to have one or more openings in the sheet. In some forms, a sheet or other structure will be provided, and one or more openings will then be formed in the sheet. Forming an opening in a material or otherwise reshaping or manipulating a material can be accomplished in a variety of ways including some that involve use of scissors, a punch, a knife or scalpel, a laser cutter or any other suitable instrumentation known for affecting the shape or configuration of a material.

Another illustrative graft element 64 useful in certain aspects of the present invention is shown in FIG. 6C. This disk-like member includes a plurality of cuts or slits 65 which are evenly spaced from one another around the circular element and which extend radially inward from the perimeter edge of the member. The cuts stop short of a circular opening that extends through the center of the graft element so as to create flaps of material between the adjacent cuts. Additionally or alternatively, slits could be made to extend out from the opening toward the periphery of the graft element. Such slits could provide reliefs in the material around the opening, for example, to facilitate receipt of the graft element over an elongate member whose diameter is greater than that of the main opening. These or similar reliefs might be useful when receiving the graft element over particular types and sizes of elongate members that would otherwise cause damage to the graft material.

Figure 6D:
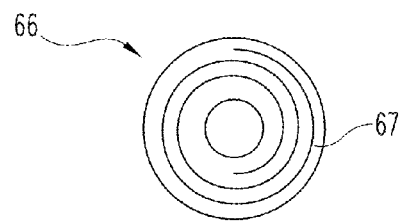
FIG. 6D is a top view of a graft element according another embodiment of the present invention.

Still another illustrative graft element 66 is shown in FIG. 6D. An ingrowth channel 67 extends in a spiraltive manner across the top surface of the member. This sort of channel or pathway can have a variety of sizes and non-spiral shapes as well, and in this regard, it will be understood that various patterns and arrangements of channels and similar adaptations can be formed. Such adaptations may extend across the entirety of the graft or be limited to interior or perhiperal regions of the article. In preferred forms, a channel will extend only partway into the surface of the material. Such a channel can be formed by making one or more cuts, scores, thinner portions, etc. in the material, for example, to form a line or channel. Such adaptations will generally be effective to create new edge or partial-thickness edge portions in the material and thereby provide further access to interior regions of the material. These types of adaptations can be incorporated into an article in a variety of ways. Illustratively, in certain embodiments, an article will be originally constructed (e.g., in a mold, extruded, etc.) with one or more of these adaptations already incorporated into the article. However, when such adaptations are incorporated into an already-existing article, they can be provided using a variety of techniques and instruments, for example, with scissors, knives, lasers such as in laser cutting or etching, or employing any number of other tools or instruments. Forming these types of adaptations may or may not involve eliminating small portions of material from the article.

Figure 8:
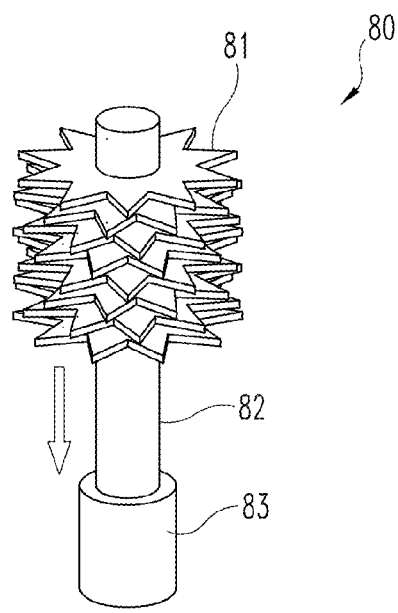
FIG. 8 is a partial, perspective view of a graft product according to another embodiment of the present invention.

Referring now to FIG. 8, shown is a partial, front view of another illustrative graft product 80 according to particular aspects of the present invention. Product 80 has some features in common with the graft product of FIG. 3B including incorporating a plurality of sheet segments 81 received over an elongate generally cylindrical graft body 82. However, in this specific illustrative embodiment, an enlarged retention portion 83, which is effective to prevent the sheet segments from passing over that end of the graft body, is located on at least one end of the graft body 82. While not necessary to broader aspects of the invention, such a retention portion might have one or more features in common with the capping members described elsewhere herein. For example, when a graft body is equipped with an enlarged end such as portion 83, this end and any other part of the graft body may be formed as a single unit (e.g., from an amount of the same material), or alternatively, such constituent components may be formed separately and then combined with one another, for example, using an adhesive, by suturing, using mechanical fastener(s), and/or any other suitable joining means. When formed separately, any two such graft components may or may not be comprised of the same material(s).

Figure 9:
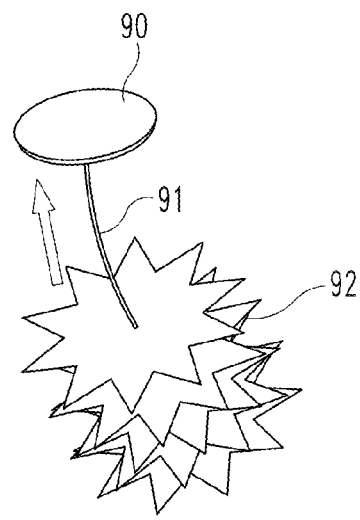
FIG. 9 is a perspective view a graft product being assembled according to one embodiment of the present invention.

Referring now to FIG. 9, shown is an example of how an illustrative graft product might be assembled according to another embodiment of the present invention. This particular graft product includes a disk-like capping member 90 having a generally circular shape, and an elongate suture 91 that extends away from the capping member. Several sheet segments 92, which are similar to those appearing in FIG. 3A except that they are being threaded onto a suture.

Figure 10:
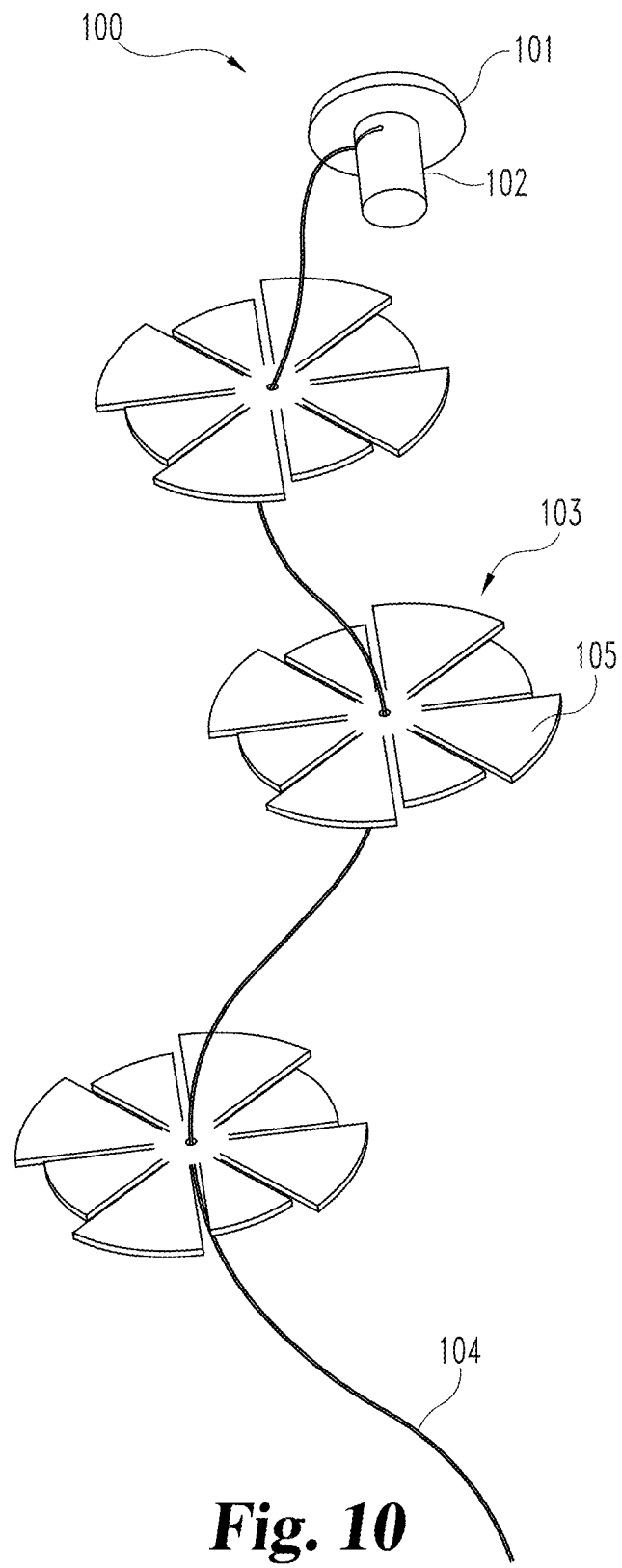
FIG. 10 is a perspective view of another inventive graft product.

With reference now to FIG. 10, shown is another illustrative graft product 100 of the present invention. This particular graft product includes a disk-like capping member 101 having a generally circular shape, and a generally cylindrical plug body 102 that extends away from the capping member. In some embodiments, the capping member will incorporate a collagenous material such as an ECM material coated with a biodegradable synthetic polymeric material (e.g., PLGA). Several sheet segments 103 are threaded onto a suture 104 which is attached to at least one of the capping member and the cylindrical plug body. Each of the segments 103 includes a plurality of generally triangular, wedge-shaped portions 105 which extend from an interior region of the segment.

Figure 11:
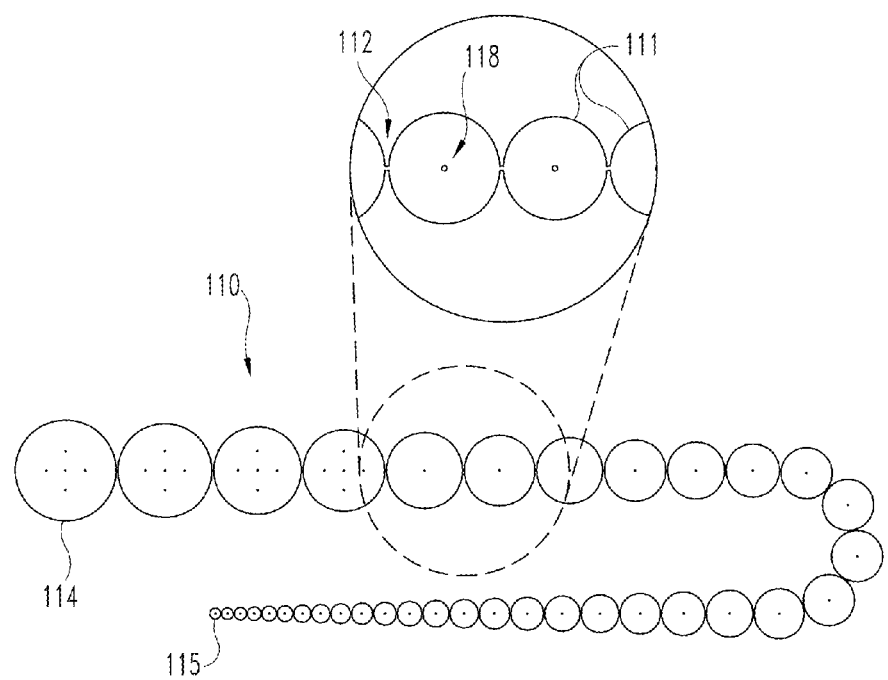
FIG. 11 is a top view of a plug-building device according one embodiment of the present invention.

In further aspects of the present invention, a plurality of sheet-like segments are taken from a single piece of donor material, and the segments are obtained such that they remain connected to one another in the obtained structure so as to provide a unitary plug-building device. FIG. 11 shows a unitary plug-building structure 110 according to one aspect of the present invention. Structure 110 reveals just one illustrative pattern by which a plurality of sheet-like segments 111 can be taken from a larger sheet of donor material. Such a unitary structure can be obtained with more or fewer sheet-like segments. In this instance, the graft segments are generally circular, and they are interconnected by bridge portions 112 extending between adjacent segments. Such graft elements can exhibit any suitable circular or non-circular shape as described elsewhere herein. Also, having these particular bridge portions, or any bridge portions, is optional. In alternative designs, the bridge portions will exhibit other suitable shapes, or there will be no discernable bridge portion between adjacent graft elements yet they will be connected to one another.

Figure 12:
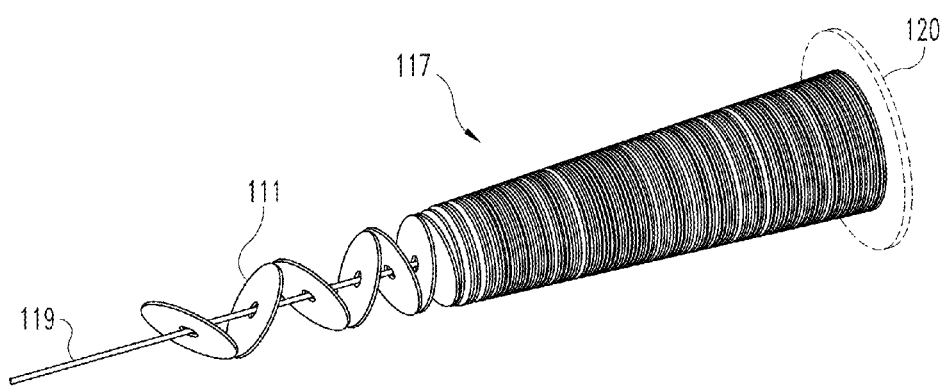
FIG. 12 is a perspective view of an inventive product incorporating the plug-building device of FIG. 11.

Continuing with FIG. 11, the sheet-like segments 111 steadily decrease in diameter moving from a first end 114 to a second end 115 of the structure. By successively folding the segments back and forth upon themselves along the bridge portions (e.g., in an accordion-like fashion), an elongate, plug-like implant 117 can be assembled as shown in FIG. 12 in which the folded segments are stacked in a generally longitudinal direction along the implant. The changing diameter of the circular segments 111 in the pre-plug structure produces a gradual taper along the implant 117 once assembled. In some embodiments, each of the graft elements within a larger unitary structure will be essentially identical in size and shape, although it will be understood that any suitable pattern, arrangement or combination of graft elements can be devised. In this regard, where a unitary plug-building structure includes multiple sheet or sheet-like graft elements any one element might vary with respect to another element in terms of its size, shape and/or any other physical or other characteristic. Accordingly, assembled implant bodies can have a constant or varying cross-sectional area along their lengths. Illustratively, an implant body, or any portion thereof, can exhibit a generally cylindrical shape, a conical shape or any other suitable shape including some that have tapered and/or non-tapered longitudinal portions. This will produce alternating large- and small-diameter portions in some assembled implant bodies. Also, a single implant can incorporate multiple, separate plug-building structures like structure 110, for example, where two or more such structures are strung along a suture or other line.

Referring again to FIG. 11, such a unitary plug-building structure can be obtained from, or otherwise formed with, any of the naturally-derived or non-naturally-derived (e.g., synthetic polymeric) materials described herein. While not necessary to broader aspects of the invention, plug-building structure 110 is formed with an ECM material (e.g., obtained from a larger sheet of ECM material that incorporates one or more individual ECM layers as described herein). In this instance, the desired length of the eventual implant in combination with size constraints imposed by the donor ECM material requires the curvature seen in the illustrated pattern. However, as discussed above, any suitable pattern or arrangement of sheet or sheet-like segments can be employed in the design of an inventive unitary plug-building structure. For example, in other instances, a unitary structure will include sheet-like segments extending in a generally straight path and/or any other shaped path along the structure.

Each of the sheet-like segments 111 is optionally equipped with a central opening 118 through which a relatively thin elongate element 119 can be received as shown in the nearly-assembled implant of FIG. 12. Such an elongate element is optional and can aid in the stacking of the elements prior to, or during, deployment at an implant site. The unitary nature of the plug-building structure 110 allows the individual sheet-like elements to remain at least temporarily connected to one another irrespective of the receiving element 119. With the stacked segments being folded back and forth upon themselves along the bridge portions 112, the bridges in some designs and with some materials can act as hinge or spring-like members between adjacent sheet-like segments, and in this regard, can enhance certain lateral flexibility features of the assembled elongate implant device. Alternative embodiments provide a plug-like body that looks similar to that shown in FIG. 12 except that the sheet-like or other graft elements are initially discrete pieces, and separately-provided bridge portions (e.g., suture, material pieces, single- or multiple-part devices) are used to connect successive sheet-like segments to construct a suitable plug-building structure.

Optionally, for certain treatment applications such as the treatment of a fistula, the implant 117 will additionally incorporate a capping member 120 (shown in phantom) from which the plurality of graft elements will extend along the elongate element 119, although an anchorable element such as elongate element 119 can be anchored in the body in a variety of fashions including some that utilize glues or other bonding agents, tissue welding techniques, friction fitting or lodgment of an anchoring member, use of hooks, barbs, pins, single- and multiple part fasteners and/or other suitable anchoring modes as discussed elsewhere herein. Near the first end 114 of the structure the first four sheet-like segments each include four additional openings around the central opening 118 which can accept suture material or the like for anchoring the capping member 120 to the stacked segments. Also, any number of additional openings can be formed in any of the sheet-like segments, for example, where openings are placed near the peripheries of certain segments to accept suture material and/or other marker-like objects for use in a direct visual or radiographic imaging operations to confirm the location of a certain region of the assembled implant device upon delivery.

Continuing with FIG. 12, capping member 120 in this illustrative embodiment is generally disc-shaped, and when adapted for treating a fistula, it can be sized for contacting portions of a tissue wall adjacent an opening to the fistula so as to inhibit its passage through the fistula opening. Such members can be formed with one or more of a variety of biodegradable and/or non-biodegradable materials as discussed elsewhere herein. In some preferred forms, the anchorable body is configured to at least partially block off fluid flow through the opening, and in some instances, to essentially seal off the opening from the passage of fluid. In some cases, holding capping member 120 in place over the fistula opening will be accomplished, at least in part, by applying tension to elongate structure 119 and maintaining this tension. In some embodiments, the capping member will incorporate a collagenous material such as an ECM material coated with a biodegradable synthetic polymeric material (e.g., PLGA).

Turning now to a more detailed discussion of materials that can be utilized in the present invention, as discussed elsewhere herein, inventive constructs can incorporate naturally derived and/or non-naturally derived materials. In this regard, one or more components of an inventive construct may comprise one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly (glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, and polyphosphazenes. These or other bioresorbable materials may be used, for example, where only a temporary function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, inventive constructs can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

In certain embodiments, one or more device components will be comprised of a remodelable material. Particular advantage can be provided by devices that incorporate a remodelable collagenous material. Such remodelable collagenous materials, whether reconstituted or naturally-derived, can be provided, for example, by collagenous materials isolated from a warm-blooded vertebrate, especially a mammal. Such isolated collagenous material can be processed so as to have remodelable, angiogenic properties and promote cellular invasion and ingrowth. Remodelable materials may be used in this context to promote cellular growth on, around, and/or in bodily regions in which inventive devices are implanted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. In a dry state, a typical layer thickness for an as-isolated submucosa or other ECM tissue layer used in the invention ranges from about 30 to about 160 microns when fully dry, more typically from about 30 to about 130 microns when fully dry.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

In certain forms, inventive devices include a material receptive to tissue ingrowth. Upon deployment of such devices in accordance with the present invention, cells from the patient can infiltrate the material, leading to, for example, new tissue growth on, around, and/or within the device. In some embodiments, the device comprises a remodelable material. In these embodiments, the remodelable material promotes and/or facilitates the formation of new tissue, and is capable of being broken down and replaced by new tissue. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical graft product of the invention (including any ECM material) might have a particular level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

Turning now to a discussion of three-dimensionally stable materials that can be incorporated into inventive grafts, and components thereof (e.g., plug body 36, graft elements 51, etc.), in accordance with some aspects of the present invention, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collageneous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wetability and rapid hydration and expansion of closure devices of the invention.

Preferred sources of collagen for forming sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming graft bodies can be highly dense, typically having densities of at least about 0.05 g/cm$^3$, preferably in the range of about 0.05 g/cm$^3$ to about 0.2 g/cm$^3$, and more preferably about 0.075 g/cm$^3$ to about 0.2 g/cm$^3$. The compacted sponge matrix can have sufficient rigidity to be deployed by passage through bodily vessels, needles, catheters or sheaths, such as by utilizing a push rod or other pusher element to force the sponge matrix body through the needle and/or catheter cannula for example. Expanded sponge densities (dry) will generally be less than the corresponding compacted densities. Typical expanded densities (dry) will range from about 0.01 g/cm³ to about 0.1 g/cm³, more preferably about 0.02 g/cm³ to about 0.07 g/cm³.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in embodiments of the invention, reference can be made, for example, to U.S. Pat. App. Pub. No. 2003/0013989.

In additional embodiments, graft elements useful in the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100×magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of graft elements useful in certain inventive devices. Methods for preparing such elements can include contacting an ECM or other collagenous starting material with an alkaline substance in an amount effective to expand the material, casting or otherwise forming the expanded collagenous material into a particular shape (e.g. an elongate tube or cylinder or a sheet-like segment), and lyophilizing the expanded material to form a dried graft body.

Products and methods of the invention can be used to treat a variety of fistulae and other passages and openings in the body. In some preferred aspects, products and methods are adapted for treating fistulae having at least a primary opening and a fistula tract extending therefrom, for example, a primary opening in the alimentary canal. Some fistulae to be treated will have at least a first fistula opening, a second fistula opening and a fistula tract extending therebetween. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae.

In this regard, inventive products and methods may be useful to treat urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae. Inventive products and methods can be used to treat a fistula regardless of its size and shape, and in some forms, are utilized to treat a fistula having a primary opening, secondary opening, and/or fistula tract with a diameter ranging from about 1 millimeter to about 20 millimeters, more typically from about 5 millimeters to about 10 millimeters.

Additionally, in some instances, a fill substance will be delivered to a fistula tract or other bodily location to accompany a graft construct that has been, or will be, deployed there. In some instances, a fill substance will reside in treatment location for a relatively short period of time such as where the fill substance is an aqueous medium (e.g., an antimicrobial mixture) that is used to flush a fistula tract, optionally followed by the introduction of one or more other fill substances or devices into the tract. In some other embodiments, steps will be taken so that a fill material remains in the tract for a somewhat lengthier period of time, in some cases indefinitely. This might involve blocking off or closing a fistula opening so that a fill device or material is prohibited from passing through the opening. Illustratively, a fistula tract can be filled with a flowable material, and opposite ends of the tract can be closed off so that the flowable material remains trapped there. In some aspects, a capping member will be used in this regard to cap off a fistula opening, and this capping member will optionally incorporate an access port that provides access through the capping member for supplying additional fill material to the tract as needed or desired.

Suitable fill substances include various space filling materials such as remodelable or resorbable materials, for example, a comminuted, fluidized, and/or gelatinous remodelable material as described elsewhere herein, or other substances (e.g., in the form of fluids, pastes, gels, sponges, powders, tissue fragments, segments, strips, layers, etc.), therapeutic agents, e.g. suitable drugs such as antibiotics, antimicrobial agents or the like. Other options include but are not limited to polymer, contrast medium, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof. As well, a plug or other material might be coated with one or more substances such as a drug coating, adhesive, sclerosant or the like.

Additionally, inventive products and methods can be used to occlude, block, fill, plug and/or otherwise treat a variety of vascular (e.g., arterial, venous, etc.) and non-vascular openings and passageways in the body. In some instances, an inventive device will be configured for placement in a naturally occurring location in the body, for example, in a native lumen or other open space in a bodily system, e.g., in an organ or other component of the circulatory, respiratory, digestive, urinary and reproductive, sensory, or endocrine systems. In certain aspects, a space to be occupied by an inventive graft is one that exists naturally in the body but relates to a disease, defect, deformation, etc. Alternatively, an opening or passageway to be occupied might be one resulting from an intentional or unintentional trauma to the body including but not limited to some relating to vehicular accidents, gunshots and other similar wounds, etc., as well as some resulting from the passage of a medical instrument (e.g., a needle, trocar, etc.) through cutaneous, subcutaneous, and/or intracutaneous tissue.

An implantable component might also include one or more radiopaque and/or ecogenic markers or a radiopaque coating or impregnation to assist in visualization of the component during a procedure. For example, radiopaque substances containing tantalum, barium, iodine, or bismuth, e.g. in powder form, can be coated upon or incorporated within an anchoring member or fill material, such that, for example, the location of the anchoring member or fill material within a patient's body can be detected.

The present invention also provides, in certain aspects, a line of medical products, wherein a medical product of the invention includes one or more devices, apparatuses or systems of the invention in a sealed package. In some forms of the invention, medical products are provided that include one or more inventive devices or systems enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical product, comprising:
   a medical implant enclosed within sterile medical packaging;
   said medical implant, while enclosed within said sterile medical packaging, comprising a capping member and an elongate implant body that includes a plurality of sheet segments, each of said sheet segments having a length, a width, a thickness, a top surface, a bottom surface and at least one side edge, said at least one side edge of a sheet segment defining the thickness and having a greater surface porosity than said top surface and said bottom surface of the same sheet segment and said at least one side edge is transverse to said top and bottom surfaces and extends from said top surface to said bottom surface, the plurality of sheet segments being stacked in a generally longitudinal direction along the length of the implant body;
   wherein the bottom surface of at least one sheet segment is in contact with the top surface of another sheet segment;
   wherein both the length and the width are greater than the thickness for each of the sheet segments; and
   wherein said capping member has a surface extending laterally away from the side edges of the sheet segments and arranged for contacting portions of a tissue wall adjacent to a fistula opening so as to inhibit passage of the capping member through the fistula opening.

2. The medical product of claim 1 further comprising an elongate element over which said sheet segments are received.

3. The medical product of claim 2, wherein said elongate element includes a generally cylindrical body having a diameter in the range of about 3 mm to about 10 mm.

4. The medical product of claim 1, wherein each of said sheet segments generally has a thickness in the range of about 0.2 mm to about 2 mm.

5. The medical product of claim 1, wherein each of said sheet segments includes a multilayered construct incorporating 2 to about 10 layers of material.

6. The medical product-of claim 1, wherein said 2 to about 10 layers of material are fused to one another.

7. The medical product of claim 1, wherein said elongate implant body has a length in the range of about 2 cm to about 20 cm.

8. The medical product of claim 1, wherein said elongate implant body has a maximum width in the range of about 4 mm to about 24 mm.

9. The medical product of claim 1, wherein the plurality of sheet segments includes about 2 stacked sheet segments per centimeter to about 30 stacked sheet segments per centimeter along the length of the implant body.

10. The medical product of claim 1, wherein the plurality of sheet segments includes about 4 stacked sheet segments per centimeter to about 12 stacked sheet segments per centimeter along the length of the implant body.

11. The medical product of claim 1, wherein said plurality of sheet segments includes a first sheet segment and a second sheet segment, the first sheet segment having a greater density than the second sheet segment.

12. The medical product of claim 11, wherein said first sheet segment and said second sheet segment comprise an extracellular matrix material.

13. The medical product of claim 1, wherein at least one of said sheet segments comprises an extracellular matrix material layer harvested in layer form from a biological tissue source.

14. The medical product of claim 1, wherein each of said sheet segments includes a plurality of openings therein extending between said top surface and said bottom surface.

15. The medical product of claim 14, wherein said plurality of openings includes a plurality of slits providing a mesh pattern.

16. The medical product of claim 1, wherein the plurality of stacked sheet segments includes successive sheet segments connected to one another.

17. The medical product of claim 16, wherein said successive sheet segments are discrete segments connected to one another with a separate connecting material.

18. The medical product of claim 16, wherein said successive sheet segments are provided by a unitary sheet structure.

19. The medical product of claim 18, wherein said unitary sheet structure is folded back and forth upon itself in the elongate implant body.

20. The medical product of claim 16, wherein said successive sheet segments comprise a first portion of a first sheet segment connected to a second portion of a second sheet segment;
wherein said first and second portions have a cross-sectional dimension that is less than a maximum cross-sectional dimension of said first and second sheet segments.

21. The medical product of claim 16, wherein said successive sheet segments are connected to one another by at least one connecting portion having a maximum cross-sectional dimension that is less than a maximum cross-sectional dimension of said successive sheet segments.

22. A method for filling at least a segment of a bodily passageway of a patient, comprising:
providing a medical implant comprising a capping member and an elongate implant body that includes a plurality of sheet segments, each of said sheet segments having a length, a width, a thickness, a top surface, a bottom surface and at least one side edge, said at least one side edge of an individual sheet segment defining the thickness and having a greater surface porosity than said top surface and said bottom surface of that individual sheet segment and said at least one side edge is transverse to said top and bottom surfaces and extends from said top surface to said bottom surface, the plurality of sheet segments being stacked in a generally longitudinal direction along the length of the implant body so as to form a stacked configuration with contacting sheet segments;
inserting, with the sheet segments in the stacked configuration, said elongate implant body into the patient;
locating said elongate implant body in the bodily passageway; and
contacting a surface of said capping member with portions of a tissue wall adjacent to an opening to the bodily passageway, said surface of the capping member extending laterally away from the side edges of the sheet segments so as to inhibit passage of the capping member through the opening;
wherein both the length and the width are greater than the thickness for each of the sheet segments.

23. The method of claim 22, wherein said bodily passageway is a fistula.

24. A medical product, comprising:
a medical implant enclosed within sterile medical packaging;
said medical implant, while enclosed within said sterile medical packaging, comprising a capping member and a plurality of material layers stacked adjacent one another in succession and held together as a stack to provide an elongate implant body for subsequent implantation in the body of a patient, the stack extending in a generally longitudinal direction along the implant body with adjacent edges of the stacked layers forming a substantial portion of a side exterior surface of the implant body;
wherein each of said material layers has a length, a width, a thickness, a top surface, a bottom surface and at least one side edge, said at least one side edge of a material layer defining the thickness and having a greater surface porosity than said top surface and said bottom surface of the same material layer;
wherein said stack includes a piece of material folded back and forth upon itself;
wherein both the length and the width are greater than the thickness for each of the material layers; and
wherein said capping member has a surface extending laterally away from the side edges of the stacked layers and arranged for contacting portions of a tissue wall adjacent to a fistula opening so as to inhibit passage of the capping member through the fistula opening.

25. The medical product of claim 24, wherein said material layers are bonded to one another.

26. A medical product, comprising:
an implantable plug device enclosed within sterile medical packaging;
said implantable plug device, while enclosed within said sterile medical packaging, comprising a stack of material layers with each of the layers having a length, a width, a thickness, a top surface, a bottom surface and a perimeter edge that defines the thickness and separates the top surface from the bottom surface, the stack extending in a generally longitudinal direction along the length of the plug device so that the perimeter edges of the stacked layers extend in a generally lateral direction across the plug device with the combined perimeter edges forming a substantial portion of the side exterior surface of the plug device; and
said perimeter edge of at least one material layer having a greater surface porosity than said top surface and said bottom surface of the same material layer;
wherein the bottom surface of at least one material layer is in contact with the top surface of another material layer;
wherein a material of the top surface of at least one material layer extends through the material layer to the bottom surface of the same material layer; and
wherein both the length and the width are greater than the thickness for each of the material layers.

27. The medical product of claim 26, wherein the combined perimeter edges of the stacked layers provide more than 50% of the side exterior surface of the plug device.

28. The medical of claim 26, wherein the combined perimeter edges of the stacked layers provide at least 90% of the side exterior surface of the plug device.

29. A medical product, comprising:
a medical implant enclosed within sterile medical packaging;
said medical implant, while enclosed within said sterile medical packaging, comprising an elongate three-dimensional plug member providing an elongate element and a capping member; and
a plurality of sheet segments each having an opening through which said elongate element can be received, the sheet segments received over the elongate element and stacked adjacent one another in succession along the elongate element such that the plurality of sheet segments extend over a substantial length of the elongate element; each of said sheet segments having a length, a width, a thickness, a top surface, a bottom surface and at least one side edge, said at least one side edge of a sheet segment defining the thickness and having a greater surface porosity than said top surface and said bottom surface of the same sheet segment;
wherein at least two sheet segments of said plurality of sheet segments are in contact with one another;
wherein said capping member has a surface extending laterally away from the side edges of the sheet segments and arranged for contacting portions of a tissue wall adjacent to an opening to the fistula so as to inhibit passage of the capping member through the fistula opening; and wherein both the length and the width are greater than the thickness for each of the sheet segments.

30. The medical product of claim 29, wherein said elongate three-dimensional plug member comprises an expandable material.

31. The medical product of claim 29, wherein the elongate three-dimensional plug member and at least one of said sheet segments comprise a collagenous material.

32. The medical product of claim 29, wherein the opening in at least one of said sheet segments is non-circular.

33. The medical product of claim 29, wherein said elongate element is an inner core.

34. The medical product of claim 29, wherein said elongate element is a filament.

35. The medical product of claim 34, wherein said filament is a suture.

36. The medical product of claim 35, wherein said at least one side edge of a sheet segment is transverse to said top and bottom surfaces and extends from said top surface to said bottom surface of said same sheet segment.

37. A medical product, comprising:
a medical implant enclosed within sterile medical packaging;
said medical implant, while enclosed within said sterile medical packaging, comprising a three-dimensional implant body that includes a sheet material folded back and forth upon itself to provide a stack of sheet segments; each of said sheet segments of the stack of sheet segments having a length, a width, a thickness, a top surface, a bottom surface and at least one side edge, said at least one side edge of a sheet segment defining the thickness and having a greater surface porosity than said top surface and said bottom surface of the same sheet segment; the stack of sheet segments extending in a generally longitudinal direction along the length of the three-dimensional implant body;
wherein both the length and the width are greater than the thickness for each of the sheet segments.

38. The medical product of claim 37, wherein said three-dimensional implant body has a length in the range of about 2 cm to about 14 cm.

39. The medical product of claim 38, wherein the stack of sheet segments includes about 2 sheet segments per centimeter to about 30 sheet segments per centimeter along the length of the three-dimensional implant body.

40. The medical product of claim 38, wherein the stack of sheet segments includes about 4 sheet segments per centimeter to about 12 sheet segments per centimeter along the length of the three-dimensional implant body.

* * * * *

UNITED STATES PATENT AND TRADEMARK OFFICE
CERTIFICATE OF CORRECTION

PATENT NO.        : 9,474,514 B2                      Page 1 of 1
APPLICATION NO.   : 13/247156
DATED             : October 25, 2016
INVENTOR(S)       : Charles W. Agnew It is certified that error appears in the above-identified patent and that said Letters Patent is hereby corrected as shown below:

On the Title Page

Related U.S. Application Data (60) Sep. 22, 2010 should read -- Sep. 28, 2010 --

Signed and Sealed this
Twenty-fourth Day of January, 2017

Michelle K. Lee
*Director of the United States Patent and Trademark Office*